(12) United States Patent
Min

(10) Patent No.: US 9,233,240 B2
(45) Date of Patent: Jan. 12, 2016

(54) SYSTEMS AND METHODS FOR DETERMINING INDUCTANCE AND CAPACITANCE VALUES FOR USE WITH LC FILTERS WITHIN IMPLANTABLE MEDICAL DEVICE LEADS TO REDUCE LEAD HEATING DURING MRI

(75) Inventor: Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 2525 days.

(21) Appl. No.: 11/955,268

(22) Filed: Dec. 12, 2007

(65) Prior Publication Data

US 2013/0123876 A1    May 16, 2013

(51) Int. Cl.
| | | |
|---|---|---|
| A61N 1/37 | (2006.01) | |
| A61N 1/05 | (2006.01) | |
| G01R 33/36 | (2006.01) | |
| A61N 1/08 | (2006.01) | |

(52) U.S. Cl.
CPC .............. *A61N 1/056* (2013.01); *A61N 1/3718* (2013.01); *A61N 2001/086* (2013.01); *G01R 33/3685* (2013.01)

(58) Field of Classification Search
CPC .......................... A61N 1/36142; A61N 1/3718
USPC .......................................................... 607/37
See application file for complete search history.

(56) References Cited

U.S. PATENT DOCUMENTS

| | | | |
|---|---|---|---|
| 4,746,864 A | 5/1988 | Satoh | |
| 5,063,348 A | 11/1991 | Kuhara et al. | |
| 6,395,637 B1 | 5/2002 | Park et al. | |
| 6,871,091 B2 | 3/2005 | Wilkinson et al. | |
| 6,930,242 B1 | 8/2005 | Helfer et al. | |
| 6,944,489 B2 | 9/2005 | Zeijlemaker et al. | |
| 6,971,391 B1 | 12/2005 | Wang et al. | |
| 6,985,775 B2 | 1/2006 | Reinke et al. | |
| 2003/0050557 A1* | 3/2003 | Susil et al. | 600/424 |
| 2003/0083723 A1 | 5/2003 | Wilkinson et al. | |
| 2003/0083726 A1 | 5/2003 | Zeijlemaker et al. | |
| 2003/0144716 A1 | 7/2003 | Reinke et al. | |
| 2003/0144718 A1 | 7/2003 | Zeijlemaker et al. | |
| 2003/0144719 A1 | 7/2003 | Zeijlemaker et al. | |
| 2006/0085043 A1 | 4/2006 | Stevenson | |
| 2007/0083244 A1 | 4/2007 | Stevenson et al. | |

FOREIGN PATENT DOCUMENTS

| | | | |
|---|---|---|---|
| WO | 03037424 A2 | 5/2003 | |
| WO | 03037424 A3 | 5/2003 | |
| WO | 03063946 A2 | 8/2003 | |
| WO | 03063946 A3 | 8/2003 | |
| WO | 03063946 C1 | 8/2003 | |
| WO | 03063953 A2 | 8/2003 | |
| WO | 03063953 A3 | 8/2003 | |

* cited by examiner

Primary Examiner — Eric D. Bertram

(57) ABSTRACT

Techniques are provided for configuring filters for reducing heating within pacing/sensing leads of a pacemaker or implantable cardioverter-defibrillator that might occur due to induced currents during a magnetic resonance imaging (MRI) procedure or in the presence of other sources of strong radio frequency (RF) fields. In particular, techniques are provided for selecting inductors and capacitors for use in LC filters while taking into account the tolerances of the component devices, as well as the target impedance of the components and the particular RF frequencies to be filtered.

13 Claims, 11 Drawing Sheets

DETERMINE SUITABLE VALUES FOR THE INDUCTANCE THEN DETERMINE CORRESPONDING CAPACITANCE

308

DETERMINE SUITABLE CENTRAL VALUES ($L_0$) FOR THE INDUCTANCE OF THE LC ELEMENT BASED ON THE TARGET IMPEDANCE ($Z_0$), A RESONANT FREQUENCY ($w_0$) OF THE RF FIELDS TO BE FILTERED, AND KNOWN TOLERANCES FOR THE CAPACITANCES AND INDUCTANCES OF THE LC ELEMENT, BY IDENTIFYING A RANGE OF VALUES THAT SATISFY THE CONDITION THAT $L_0 > Z_0 * (-\Delta C/C_0 + \Delta C/C_0 * \Delta L/L_0 - \Delta L/L_0) / \omega_0(1 - \Delta L/L_0)$ WHERE $\Delta C/C_0$ IS THE TOLERANCE OF THE CAPACITANCE OF THE LC ELEMENT AND $\Delta L/L_0$ IS THE TOLERANCE OF THE INDUCTANCE OF THE LC ELEMENT

309

SELECT A PARTICULAR VALUE FOR $L_0$ WITHIN THE RANGE OF SUITABLE VALUES DETERMINED FOR $L_0$ AND THEN DETERMINE A CORRESPONDING VALUE FOR $C_0$ BASED ON:

$C_0 = 1 / (\omega_0^2 * L_0)$

FIG. 8

SYSTEMS AND METHODS FOR DETERMINING INDUCTANCE AND CAPACITANCE VALUES FOR USE WITH LC FILTERS WITHIN IMPLANTABLE MEDICAL DEVICE LEADS TO REDUCE LEAD HEATING DURING MRI

CROSS REFERENCE TO RELATED APPLICATIONS

This application is related to copending U.S. patent application Ser. No. 12/325,495, filed Jun. 3, 2010, titled "Systems and Methods for Selecting Components for Use in RF Filters Within Implantable Medical Leads Based on Inductance, Parasitic Capacitance and Parasitic Resistance".

FIELD OF THE INVENTION

The invention generally relates to leads for use with implantable medical devices, such as pacemakers or implantable cardioverter-defibrillators (ICDs) and, in particular, to systems and methods for determining inductance and capacitance values for use in inductive-capacitive (LC) filtering elements within such leads to reduce tip heating during magnetic resonance imaging (MRI) procedures.

BACKGROUND OF THE INVENTION

MRI is an effective, non-invasive magnetic imaging technique for generating sharp images of the internal anatomy of the human body, which provides an efficient means for diagnosing disorders such as neurological and cardiac abnormalities and for spotting tumors and the like. Briefly, the patient is placed within the center of a large superconducting magnet that generates a powerful static magnetic field. The static magnetic field causes protons within tissues of the body to align with an axis of the static field. A pulsed radio-frequency (RF) magnetic field is then applied causing the protons to begin to precess around the axis of the static field. Pulsed gradient magnetic fields are then applied to cause the protons within selected locations of the body to emit RF signals, which are detected by sensors of the MRI system. Based on the RF signals emitted by the protons, the MRI system then generates a precise image of the selected locations of the body, typically image slices of organs of interest.

However, MRI procedures are problematic for patients with implantable medical devices such as pacemakers and ICDs. One of the significant problems or risks is that the strong RF fields of the MRI can induce currents through the lead system of the implantable device into the tissues resulting in Joule heating in the cardiac tissues around the electrodes of leads, potentially damaging adjacent tissues. Indeed, in worst-case scenarios, the temperature at the tip of an implanted lead has been found to increase as much as 70 degrees Celsius (C) during an MRI tested in a gel phantom in a non-clinical configuration. Although such a dramatic increase is probably unlikely within a clinical system wherein leads are properly implanted, even a temperature increase of only about 80-13° C. might cause myocardial tissue damage.

Furthermore, any significant heating of cardiac tissues near lead electrodes can affect the pacing and sensing parameters associated with the tissues near the electrode, thus potentially preventing pacing pulses from being properly captured within the heart of the patient and/or preventing intrinsic electrical events from being properly sensed by the device. The latter might result, depending upon the circumstances, in therapy being improperly delivered or improperly withheld. Another significant concern is that any currents induced in the lead system can potentially generate voltages within cardiac tissue comparable in amplitude and duration to stimulation pulses and hence might trigger unwanted contractions of heart tissue. The rate of such contractions can be extremely high, posing significant clinical risks on patients. Therefore, there is a need to reduce heating in the leads of implantable medical devices, especially pacemakers and ICDs, and to also reduce the risks of improper tissue stimulation during an MRI, which is referred to herein as MRI-induced pacing.

A variety of techniques have been developed. See, for example, the following patents and patent applications: U.S. Pat. Nos. 6,871,091, 6,930,242, 6,944,489, 6,971,391, 6,985,775; U.S. Patent Application Nos. 2003/0083723, 2003/0083726, 2003/0144716, 2003/0144718, and 2003/0144719, and 2006/0085043; as well as the following PCT documents WO 03/037424, WO 03/063946, WO 03/063953. At least some of these techniques are directed to the use of RF filters, such as inductive filters or LC filters, within the leads for use in filtering RF signals induced by MRIs.

However, issues arise in determining optimal values for L and C for use within the RF filters mounted within device leads. Preferably, L and C values are selected so that the RF filter resonates at the frequency of RF signals induced by the MRI, such as at a resonant frequency of, e.g., 65.3 MHz of 1.5 T or 128 MHz of 3 T. In principle, a wide range of L and C values can potentially be used to achieve a desired resonant frequency based on: $2\pi*f=1/\sqrt{L*C}$ wherein "f" is the resonant frequency. (Solving for L, this equation may also be represented as: $L=1/(4\pi^2 f^2 C)$.) However, it has been discovered that not all combinations of permissible L and C values are equally effective in reducing lead heating.

FIG. 1 illustrates a range of L and C values for an LC filter wherein curve 1 represents combinations of values satisfying the aforementioned equations for a resonant frequency of 65.3 MHz. Any combination of L and C values along the curve satisfies the equations, such as combination $LC_1$ (where L=10 nH and C=620 pF) or combination $LC_2$ (where L=297 nH and C=20 pF). However, lead modeling and in vitro tests have shown that combination $LC_2$ achieves a significantly greater reduction in tip heating as compared to combination $LC_1$.

FIG. 2 illustrates expected increases in lead temperatures arising within a lead due to an 65.3 MHz/1.5 Tesla MRI for one in vitro lead implementation and three non in vitro lead implementations, with the expected temperature increases determined via computer modeling. In FIG. 2, the expected temperature increase within the lead is shown for various exemplary lead lengths in the range of 30-45 cm. Curve 2 represents the expected increase in lead tip temperature for a non in vitro lead during the MRI while using an LC filter with parameters $LC_2$. Curve 3 represents the expected increase in lead tip temperature for a non in vitro lead during the MRI while using an LC filter with parameters $LC_1$. Curve 4 represents the expected increase in lead tip temperature for a non in vitro lead during the MRI without an LC filter. Curve 5 represents the expected increase in lead tip temperature for an in vitro lead during an MRI, also without an LC filter. As can be seen, without an LC filter, the tip temperature is expected to increase by as much as 20 degrees C. due to the MRI (with the greatest increase expected in a 30 cm lead). Although LC filter combination $LC_1$ is expected to achieve a reduction in tip temperature during the MRI as compared to the control lead, the $LC_2$ filter combination is expected to achieve a much greater reduction in tip temperatures. Indeed, with the $LC_2$ combination, only a minimal temperature increase is expected during an MRI, regardless of lead length.

FIG. 3 illustrates increases in lead temperature measured within in vitro test leads exposed to an 65.3 MHz/1.5 T MRI. Again, temperature increases during the MRI are plotted for the two exemplary LC combinations ($LC_1$ and $LC_2$) and for a control lead without an LC filter. In FIG. 3, the measured temperature increase within the lead is shown for various exemplary lead lengths in the range of 25-53 cm. Curve 6 represents the increase in lead tip temperature measured during the MRI when employing an LC filter with parameters $LC_2$. Curve 7 represents the increase in lead tip temperature measured when employing an LC filter with parameters $LC_1$. Curve 9 represents the increase measured in lead tip temperature without an LC filter. As can be seen, without an LC filter, the tip increased by as much as 33 degrees C. due to the MRI (with the greatest increase occurring in a 25 cm lead). LC filter combination $LC_1$ achieved only minimal reductions in tip temperature during the MRI as compared to the control lead. However, the $LC_2$ filter combination achieved significant reductions in tip temperatures, up to 90% or more. Indeed, the in vitro results of FIG. 3 demonstrate that an even more significant reduction in tip temperature can be achieved when using the $LC_2$ combination than the $LC_1$ combination, as compared to the reduction shown in the modeling results of FIG. 2 for non in vitro lead models.

As can be appreciated, there is a need to understand the significant differences in lead temperature reduction achieved with different combinations of resonant LC values in practical implementations. Furthermore, there is a need to determine suitable combinations of L and C values for LC filters for use within particular implementations so as to achieve an effective reduction in lead temperature during an MRI, as compared to leads without LC filters. It is to these ends that the invention is generally directed.

SUMMARY OF THE INVENTION

In accordance with exemplary embodiments of the invention, a method is provided for identifying suitable components for use within an LC element to reduce heating within a lead of an implantable medical device due to strong RF fields, such as those arising during an MRI. In one example, tolerances for capacitances and inductances of candidate components for use in the LC element are determined. That is, various candidate inductors and capacitors are identified that have sizes, configurations and other characteristics appropriate for use in implantable medical device leads. For each candidate component, the operational tolerances are obtained from the manufacturer or are otherwise measured. Then, suitable values for the capacitance and the inductance of the LC element are determined based on the RF frequency to be filtered, the tolerances for the capacitances and the inductances of the candidate components, and a target impedance value. Typically, for RF frequencies of 65 MHz or 128 MHz, a targeted lower bound for the amplitude of the impedance of 1000 ohms is appropriate. Usually, the higher the impedance, the better the performance. Particular inductive and capacitive components are then selected from among the candidate components for use in the LC element based on the suitable capacitance and inductance values.

Hence, at least some aspects of the invention exploit the recognition that it is preferable and perhaps necessary to achieve a high target impedance, such as 1000 ohms, at the resonant RF frequency in order to achieve adequate temperature reduction during an MRI. Aspects of the invention also exploit the recognition that variations in the tolerances of inductive and capacitive components for use in an LC filtering element significantly affect the capability of the LC element to achieve the target impedance. Hence, it is not sufficient to merely select a combination of L and C components that, in theory, provide a resonant frequency corresponding to the frequency of the RF signals to be filtered. Rather, to achieve significant temperature reductions within leads during an MRI, it is necessary (or at least far preferable) to first determine suitable inductive and capacitive values while taking into account the tolerances of the component devices (as well as the target impedance and the RF frequencies to be filtered.) Then, components can be selected that will achieve the target impedance at the resonant frequency despite variations due to tolerance.

In an illustrative embodiment, a suitable target lower bound ($Z_0$) for the impedance is first input. For RF fields associated with MRIs, $Z_0$ can be set to 1000 ohms. Next, suitable values for the capacitance and the inductance of the LC element are identified by determining ranges of values that satisfy:

$$C_0 < (1-\Delta L/L_0)/[\omega_0 Z_0(-\Delta C/C_0 + \Delta C/C_0 * \Delta L/L_0 - \Delta L/L_0)]$$

or $$L_0 > Z_0*(-\Delta C/C_0 + \Delta C/C_0 * \Delta L/L_0 - \Delta L/L_0)/\omega_0(1-\Delta L/L_0)$$

where $C_0$ represents a central value for the capacitance, $L_0$ represents a central value for the inductance, $\Delta C/C_0$ represents the tolerance of the capacitance of the LC element, $\Delta L/L_0$ represents the tolerance of the inductance of the LC element, $\omega_0$ represents the resonant frequency. For each $C_0$ value found to be suitable, the corresponding $L_0$ value may then be derived based on $L_0 = 1/(\omega_0^2 * C_0)$. Conversely, for each $L_0$ value found to be suitable, the corresponding $C_0$ may then be derived based on $C_0 = 1/(\omega_0^2 * L_0)$.

Once suitable ranges of values for $L_0$ and $C_0$ have been determined, particular inductive and capacitive components are then selected from among candidate components provided by manufactures by identifying the components having central values for capacitance and inductance close to the determined values of $C_0$ and $L_0$. In one particular example, for a target impedance of 1000 ohms and assuming ±5% tolerance in inductances and capacitances and also assuming a 65.3 MHz/1.5 T MRI, suitable $C_0/L_0$ combinations are found to be in the range of 19 pF/312.65 nH to 23.7 pF/250.14 nH. Particular inductors and capacitors are then selected for use in the lead from among candidate components that meet these specifications (and which are otherwise suited for use in implantable medical leads). Hence, for example, the combination of an inductor providing 297 nH ±5% and a capacitor providing 20 pF±5% might be selected; whereas the combination of an inductor providing 10 nH ±5% and a capacitor providing 620 pF ±5% would not be suitable, although both theoretically achieve the same resonant frequency. Similarly, for 128 MHz/3.0T, the pairs such as inductor 140.5 nH ±5% and capacitor 11 pF ±5% as derived from the criteria can be selected. Where possible, a combination of components are selected so as to achieve a target impedance within the lead in the presence of MRI fields of differing RF frequencies, e.g., 65.3 MHz/1.5 T and 128 Mha/3.0 T.

Still further, it is desirable to take parasitic resistance values and parasitic capacitance values into account while selecting the inductive component. For example, parasitic resistance ($R_s$) values and parasitic capacitance ($C_S$) values are determined for candidate inductive components for use in the LC element. A particular inductive component is then selected from among various candidate components based, in part, on $R_s$ and $C_S$. In one particular example, a low target $C_s$ value is first identified. Also, the resistance of the tip stimulation electrode to be used in the lead is determined. Then, an inductive component is selected which has a sufficiently large inductance to yield the low target $C_s$ value and which also has an $R_s$ value smaller than the expected resistance of the tip stimulation electrode. The capacitive component is then selected based on the inductive component and in view of the considerations summarized above. Again, where possible, the inductive and capacitive components are selected so as to achieve a target temperature reduction within the lead in the presence of MRI fields of differing RF frequencies.

The component selection and specification techniques are particularly well suited for use with LC filtering components for use in bipolar cardiac pacing/sensing leads for use with pacemakers and ICDs but may also be employed in connection with other filtering components or for use in other types of leads or for use with other implantable medical devices. Also, the techniques described herein are applicable, where appropriate, to inductive-capacitive elements having both an inductor and a capacitor as well as to inductive-capacitive elements having an inductor with a parasitic capacitance.

BRIEF DESCRIPTION OF THE DRAWINGS

The above and further features, advantages and benefits of the invention will be apparent upon consideration of the descriptions herein taken in conjunction with the accompanying drawings, in which:

FIG. 8 is a flow diagram illustrating an exemplary method for determining ranges of suitable inductance values for use with the method of FIG. 6;

DETAILED DESCRIPTION OF THE PREFERRED EMBODIMENTS

The following description includes the best mode presently contemplated for practicing the invention. The description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of MRI System

Figure 4:
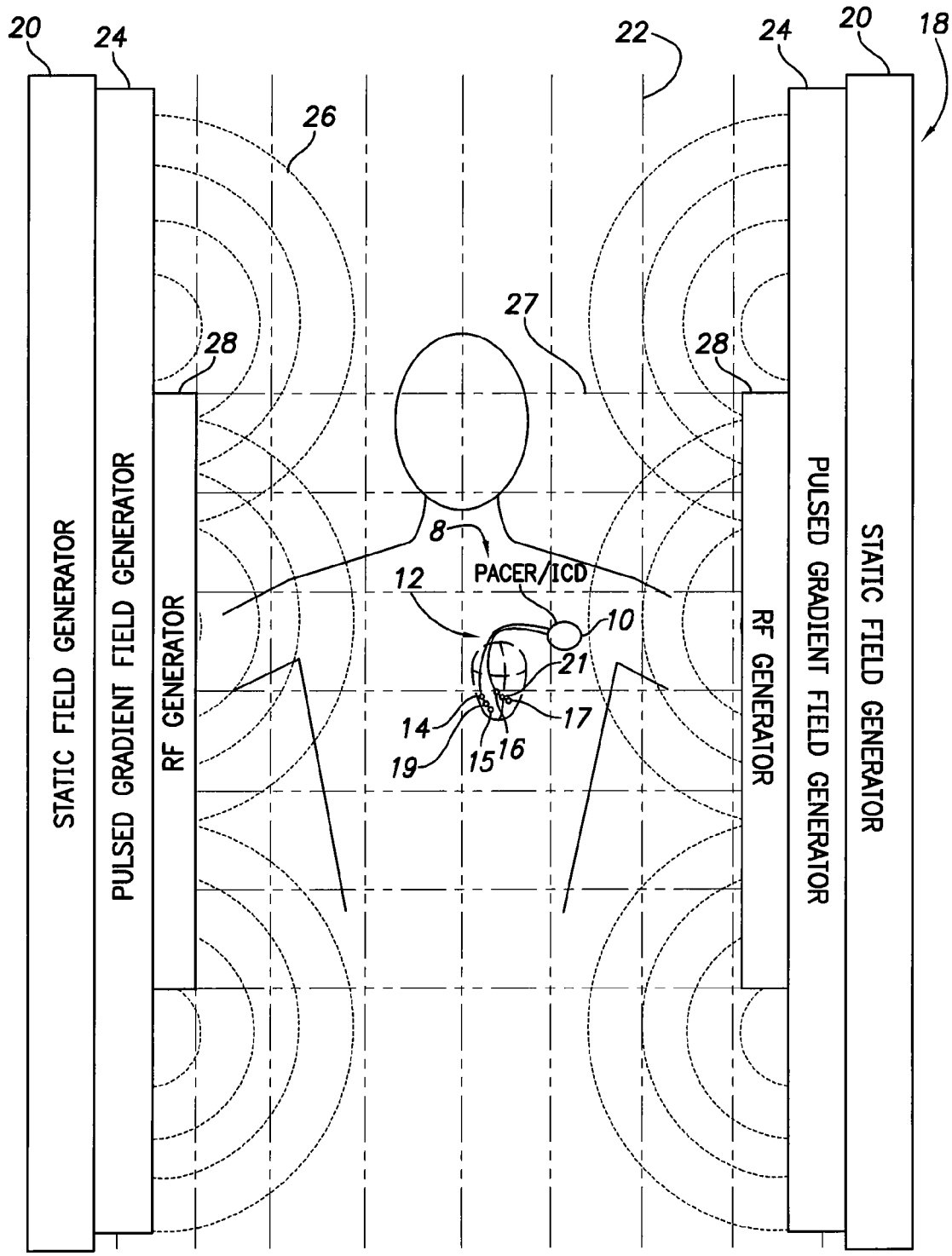
FIG. 4 is a stylized representation of an MRI system along with a patient with a pacer/ICD implanted therein with RV and LV leads employing LC filtering elements near their distal ends.
Figure 10:
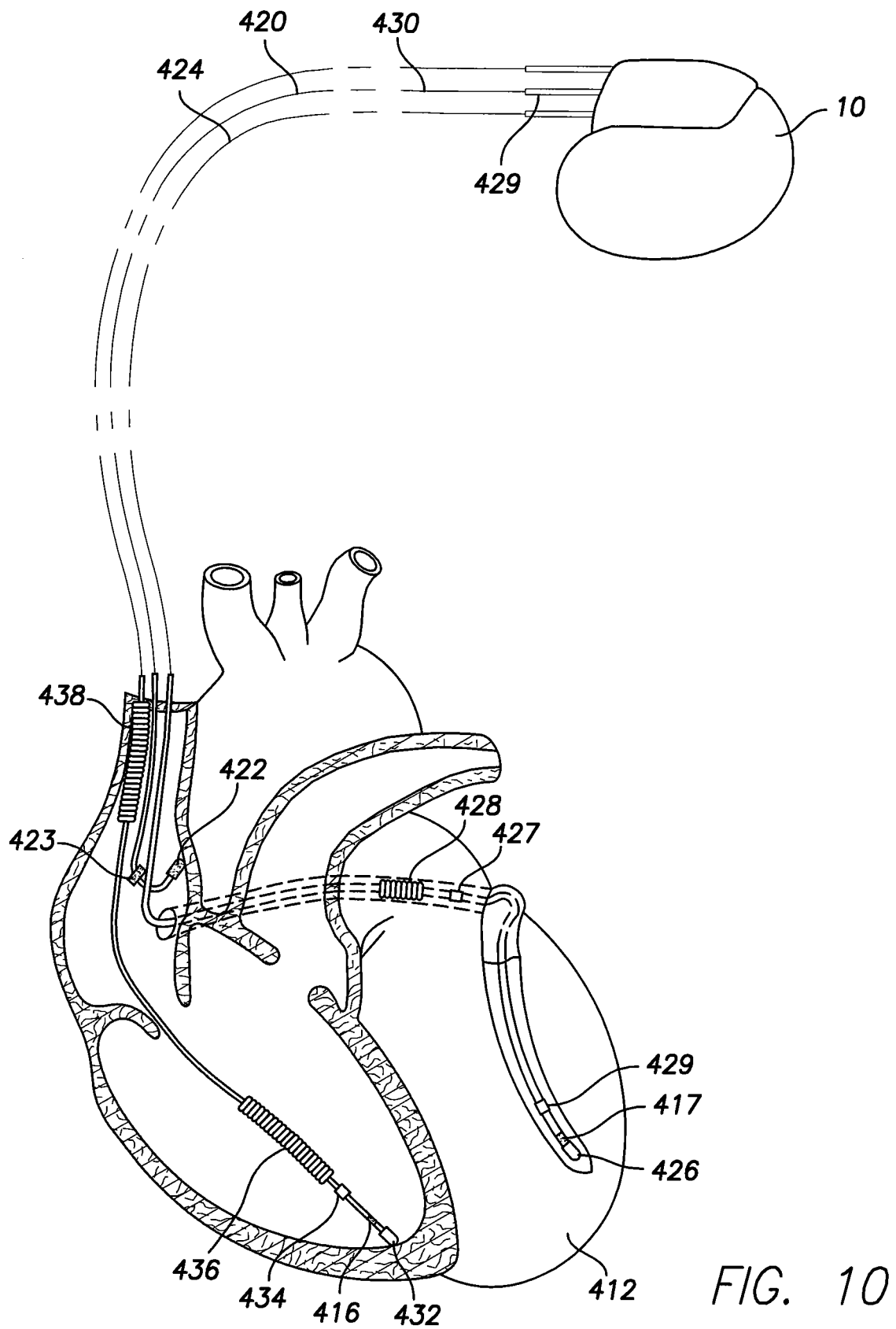
FIG. 10 is a simplified, partly cutaway view, illustrating the pacer/ICD of FIG. 1 along with a more complete set of leads implanted in the heart of the patient, wherein the RV and LV leads each include an RF filtering element near tip electrodes of the leads.

FIG. 4 illustrates an implantable medical system 8 having a pacer/ICD 10 for use with a set of coaxial bipolar pacing/sensing leads 12, which include tip and ring electrodes 14, 15, 16 and 17, as well as LC filtering elements 19 and 21 (which are internal to the lead) for use in filtering RF signals. The filtering elements are connected to the tip electrodes 15, 17 of the respective leads so as to reduce lead heating caused by loop currents generated by an MRI system 18 to further reduce or prevent improper stimulation of the heart due to such loop currents. In FIG. 4, only two leads are shown, a right ventricular (RV) lead and a left ventricular (LV) lead. A more complete lead system is illustrated in FIG. 10, described below. As will be explained further, the components of the LC filtering elements are selected during lead design so as to achieve optimal filtering of current loops induced by the RF fields of an MRI or other source of RF fields. In some implementations, one or more additional leads may be provided (such as a right atrial (RA) lead). LC filtering elements may be provided within the additional leads as well. Also, in some implementations, no LV lead is provided.

As to the MRI system 18, the system includes a static field generator 20 for generating a static magnetic field 22 and a pulsed gradient field generator 24 for selectively generating pulsed gradient magnetic fields 26. The MRI system also includes an RF generator 28 for generating RF fields 27. Other components of the MRI, such as its sensing and imaging components are not shown. MRI systems and imaging techniques are well known and will not be described in detail herein. For exemplary MRI systems see, for example, U.S. Pat. No. 5,063,348 to Kuhara, et al., entitled "Magnetic Resonance Imaging System" and U.S. Pat. No. 4,746,864 to Satoh, entitled "Magnetic Resonance Imaging System." Note that the fields shown in FIG. 4 are stylized representations of MRI fields intended merely to illustrate the presence of the fields. Actual MRI fields generally have far more complex patterns.

Lead Overview

Figure 5:
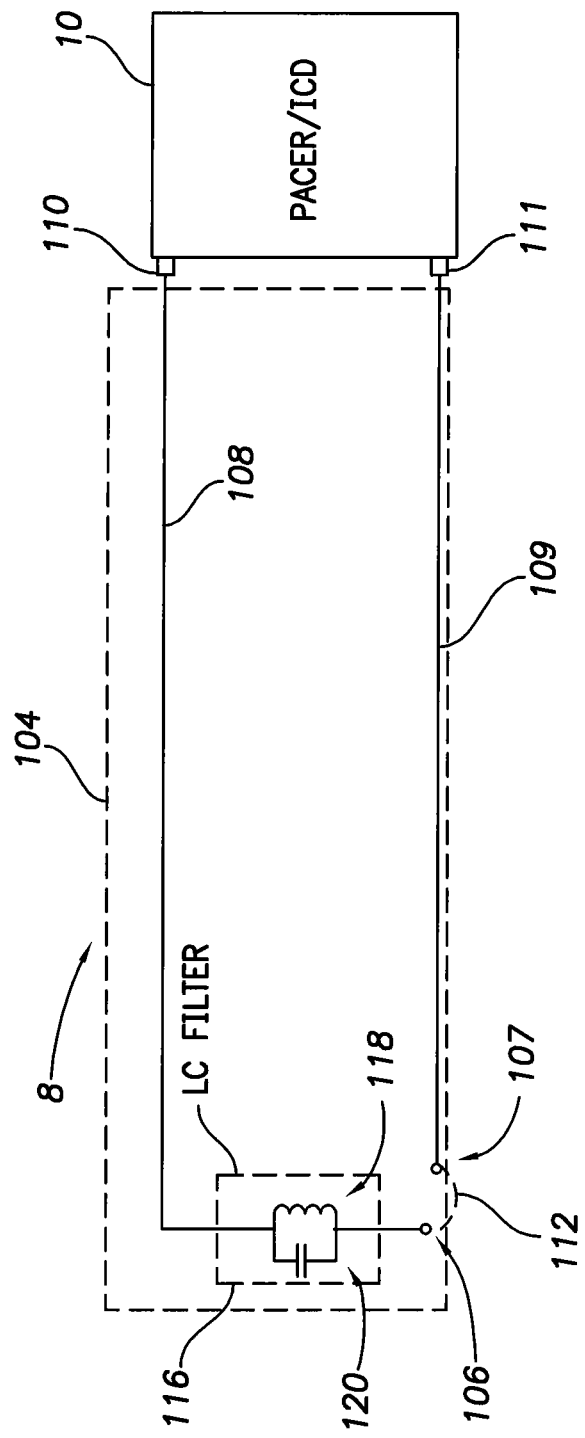
FIG. 5 is a block diagram, partly in schematic form, illustrating a bipolar lead for use with the pacer/ICD of FIG. 4 wherein an LC filtering element is mounted along a tip conductor to reduce tip heating during an MRI, and also illustrating a pacer/ICD connected to the lead.

FIG. 5 illustrates an implantable system 8 having a pacer/ICD or other implantable medical device 10 with a bipolar coaxial lead 104. The bipolar lead includes a tip electrode 106 electrically connected to the pacer/ICD via a tip conductor 108 coupled to a tip connector or terminal 110 of the pacer/ICD. The bipolar lead also includes a ring electrode 107 electrically connected to the pacer/ICD via a ring conductor 109 coupled to a ring connector or terminal 111 of the pacer/ICD. Depending upon the particular implementation, during pacing/sensing, the tip electrode may be more negative than the ring, or vice versa. A conducting path 112 between tip electrode 106 and ring electrode 107 is provided through patient tissue (typically cardiac tissue.) An LC filtering element 116 is connected along conductor 108 at a distal portion thereof near tip electrode 106. The LC filter includes, in this example, an inductor 118 and a capacitor 120. In other examples, more or fewer components may be used including, e.g., filters including only inductors but no capacitors. The LC components can be lumped or have a distributed structure.

Figure 2:
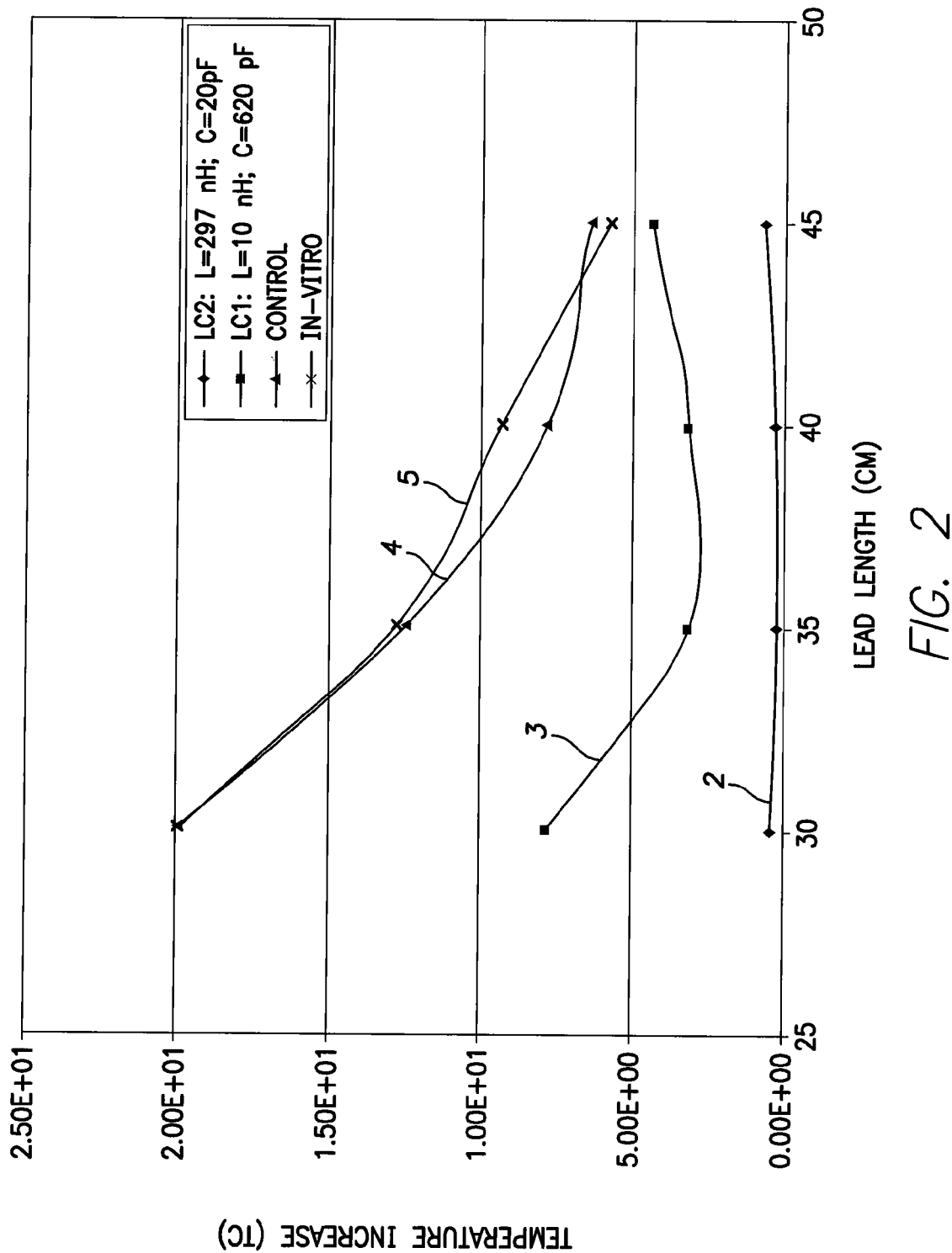
FIG. 2 illustrates expected increases in lead temperatures arising within a lead due to an 65.3 MHz/1.5 T MRI for two exemplary LC combinations and for a control lead without an LC filter.

With the lead arrangement of FIG. 2, during an MRI, one or more current loops might be induced within the lead (and within any circuit components within the pacer/ICD that electrically connect terminals 110 and 111). The LC filter is configured to filter frequencies associated with such current loops to decrease the magnitude thereof. Without the LC filter, strong current loops might pass through patient tissue between the tip and ring electrodes before returning to the pacer/ICD, causing considerable resistive heating at the electrodes and in the intervening tissue. As explained above, such heating can damage patient tissue and interfere with pacing and sensing. In addition, as noted, the current loops can cause MRI-induced pacing.

With LC filter 116, however, any such current loops are greatly diminished, thereby reducing a significant source of tip heating as well as preventing or limiting MRI-induced pacing. Although not shown, RF shielding and/or MRI responsive switches can also be provided to further reduce lead heating. Note that different types of LC filters may be provided within atrial leads as compared to ventricular leads, with the filters of ventricular leads being generally more robust than the LC filters of the atrial leads since, typically, larger currents are induced in ventricular leads than in atrial leads during an MRI. In the following, techniques will be described for selecting the particular inductive and capacitive components for use in the LC filter to achieve effective reduction in lead temperatures during an MRI within the patient or in the presence of other sources of strong RF fields.

Component Selection Overview

Figure 6:
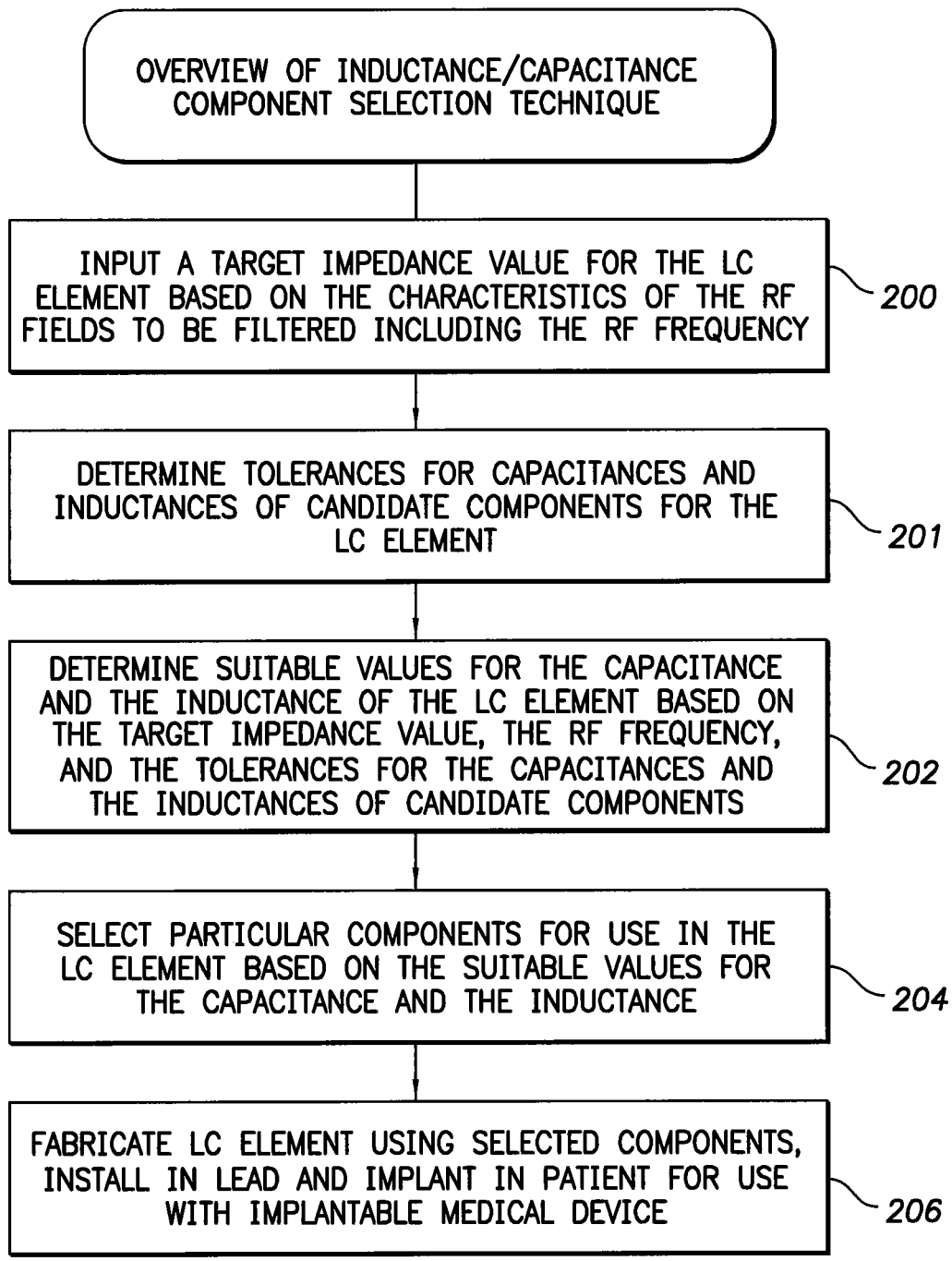
FIG. 6 is a flow diagram summarizing method for determining suitable inductance and capacitance values for use with the LC filter of FIG. 5.

Turning now to FIG. 6, a component selection overview is provided for use by lead designers while designing or configuring a lead. At step 200, a suitable impedance value for the LC element to be used in the lead is input. The impedance value may be expressed as a targeted lower bound for the amplitude of the impedance. The target value may differ based on the characteristics of the RF fields to be filtered, such as its frequency. For a 64 MHz/1.5 T MRI or a 128 MHz/3.0 T MRI, an impedance value of 1000 ohms is typically sufficient. This value was ascertained via modeling to determine an impedance value sufficient to achieve significant heat reduction (within cardiac pacing/sensing leads wherein the LC filtering components are connected in series with the tip conductor and wherein the filtering components were not subject to significant variations due to tolerance.) This value was confirmed through experimentation. Lower target impedance values may also be used, such as 800 ohms, but 1000 ohms was found to be more effective. Typically, the higher the impedance, the better. At step 201, tolerances for capacitances and inductances of candidate components for the LC element are determined with reference, for example, to manufacturer specifications. That is, candidate inductive and capacitive components for use in the LC filter of the lead are identified from among various components provided by manufactures (based, e.g., on size, weight, durability, etc.) and then the tolerances of the components are determined, e.g. with reference to manufacturer specifications or through independent testing. At step 202, suitable values for the capacitance and the inductance of the LC element are determined based on the target impedance value, the frequency of the RF fields to be filtered, and the tolerances for the capacitances and the inductances of candidate components the LC element. Exemplary techniques for determining suitable values for the capacitances and inductances will be described with reference to FIG. 7.

Figure 1:
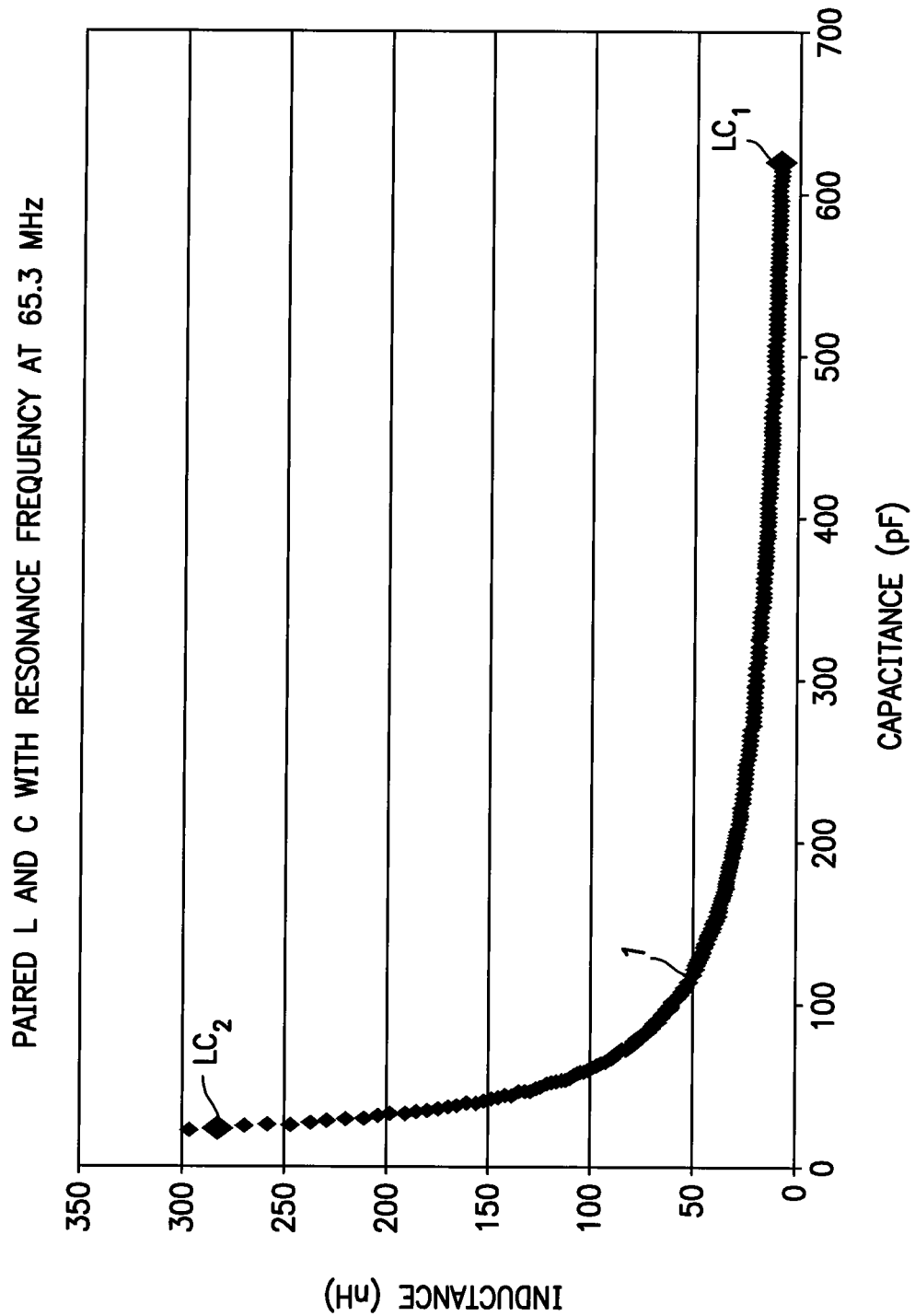
FIG. 1 illustrates combinations of L and C values theoretically achieving a resonant frequency of 65.3 MHz.
Figure 3:
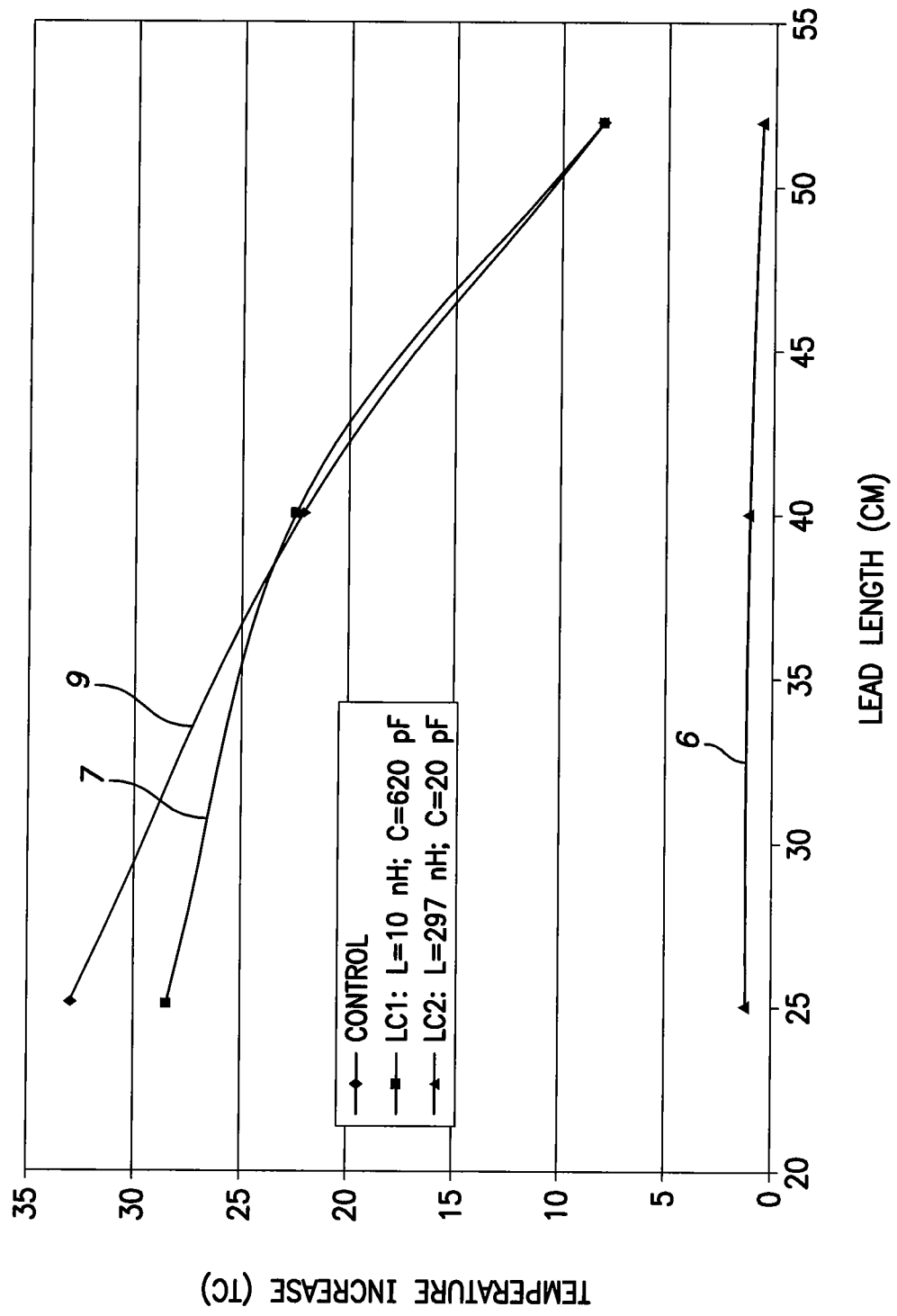
FIG. 3 illustrates measured increases in lead temperatures arising within a lead due to an 65.3 MHz/1.5 T MRI for two exemplary LC combinations and for a control lead without an LC filter.

At step 204, particular inductive and capacitive components are selected for use in the LC element of the lead based on the values for the capacitance and the inductance determined at step 202. Exemplary techniques will be described with reference to FIG. 9. Then, at step 206, LC elements are fabricated using the selected components, installed in leads and then implanted in patients for use with implantable medical devices (following suitable testing and approval procedures.) Hence, rather than merely selecting a combination of inductive and capacitive components that, in theory, provide a resonant frequency corresponding to the RF signals to be filtered, the technique of FIG. 6 operates to first determine suitable inductive and capacitive values while taking into account the tolerances of the component devices, as well as the impedance and particular RF frequencies to be filtered. Using this technique with the exemplary component combinations of FIGS. 1-3 (and assuming a ±5% tolerance in the components), combination $LC_2$ would be selected, rather than $LC_1$, yielding a substantial improvement in temperature reduction in the lead during an MRI. Note that, although the technique of FIG. 6 is primarily intended for use by engineers or other personnel while designing lead systems, the techniques may be automated (where appropriate) for use by computerized design systems or the like. Also, note that the general technique of FIG. 6 is applicable, where appropriate, to inductive-capacitive elements having both an inductor and a capacitor as well as to inductive-capacitive elements having an inductor with a parasitic capacitance. In the later case, the technique operates to identify suitable inductors having inductance and parasitic capacitance values corresponding to the suitable values determined at step 202.

DETAILED EXAMPLES

Figure 7:
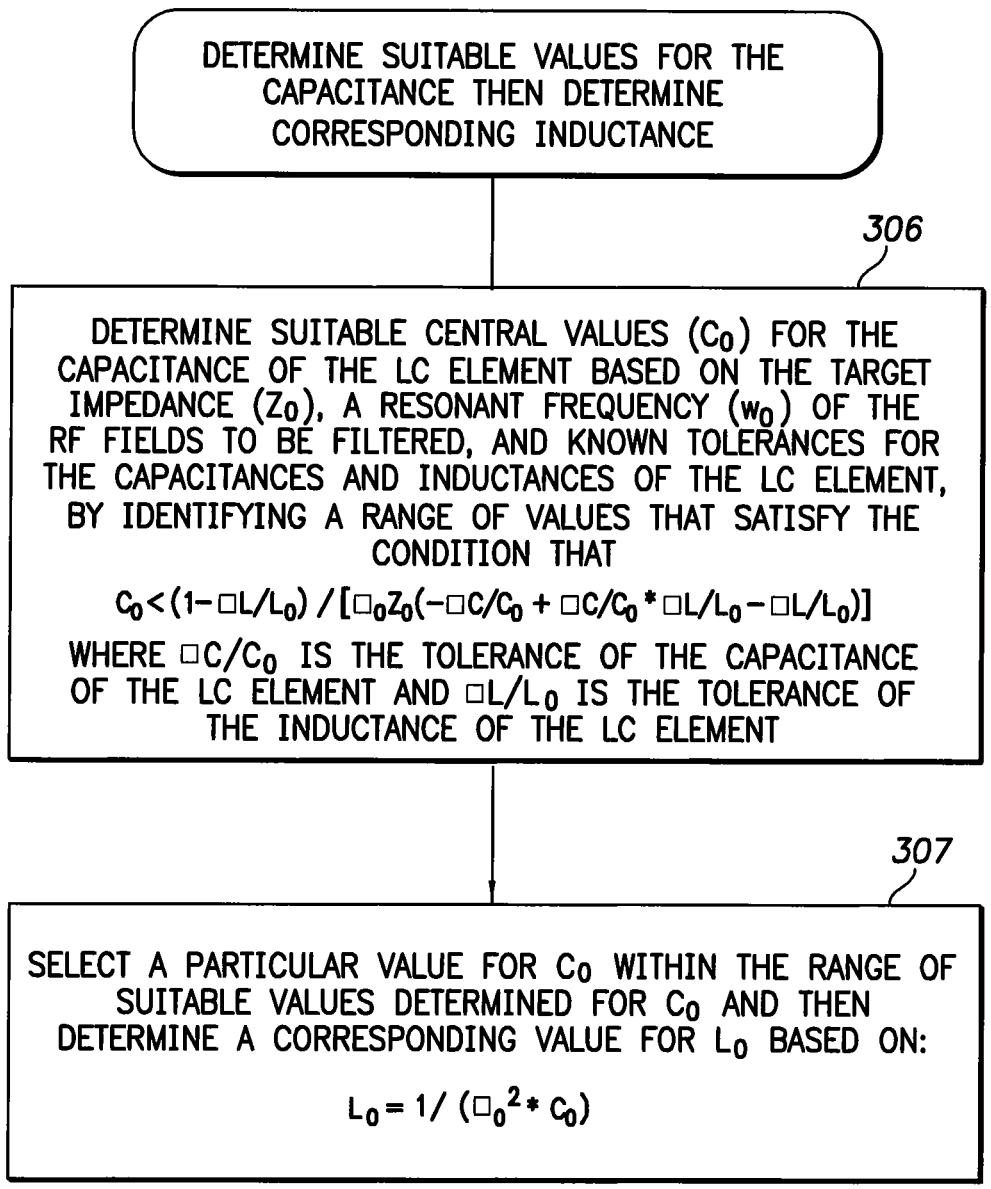
FIG. 7 is a flow diagram illustrating an exemplary method for determining ranges of suitable capacitance values for use with the method of FIG. 6.
Figure 9:
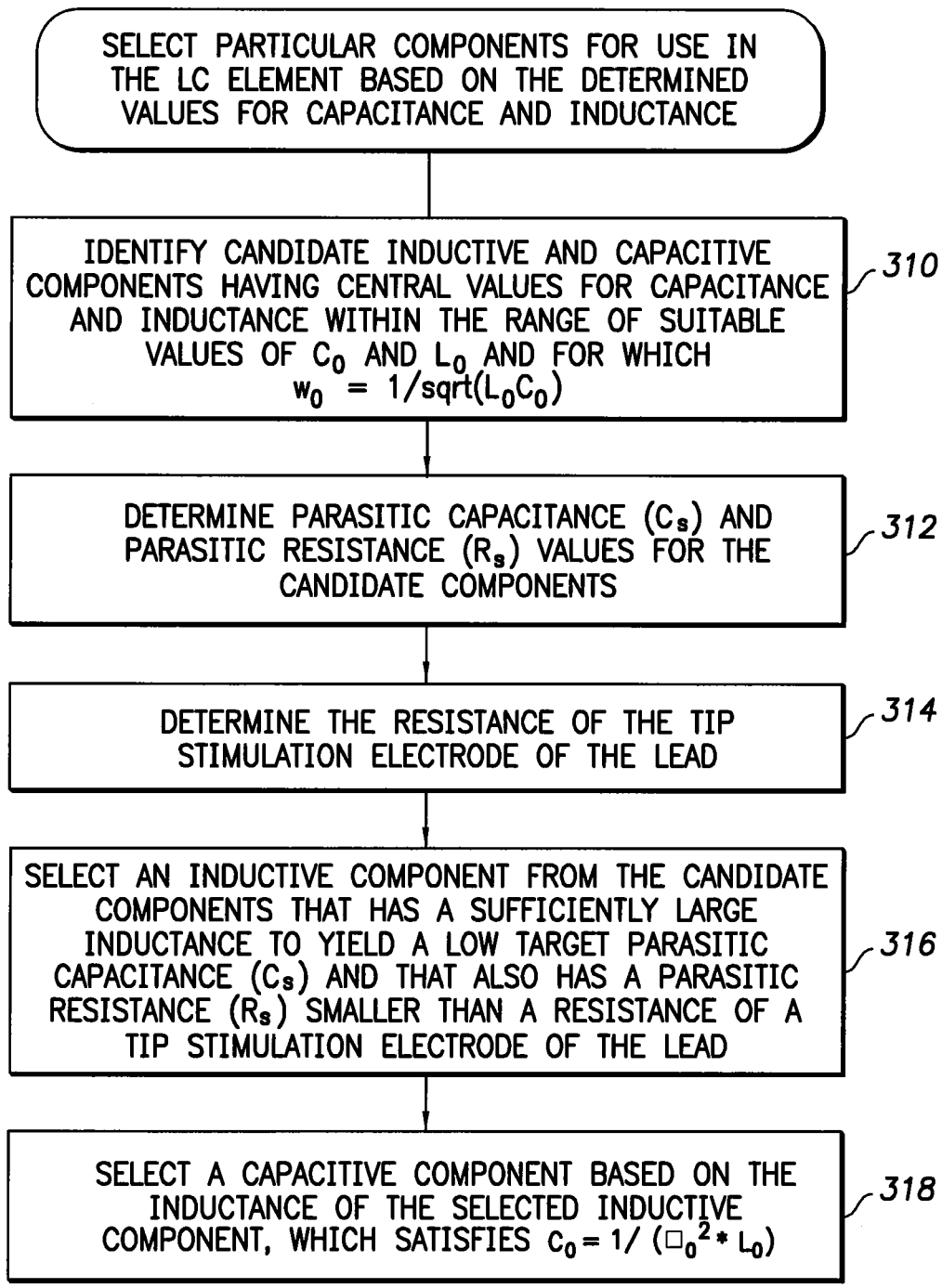
FIG. 9 is a flow diagram illustrating an exemplary method for identifying particular capacitance and inductance values for use with the method of FIG. 6, while taking into account parasitic capacitance and parasitic resistances.

Turning now to FIGS. 7-9, exemplary techniques for use with the various steps of FIG. 6 will be described. These techniques, like those of FIG. 6, are typically performed by designers of implantable medical device leads. Beginning with FIG. 7, a technique is illustrated for determining ranges of suitable values for the capacitance of the LC element based on the targeted lower bound of the amplitude of the impedance and other factors. Once the capacitance has been determined, corresponding inductance values can be calculated using $L_0=1/(\omega_0^2 * C_0)$. At step 306, a range of suitable central values ($C_0$) are determined for the capacitance of the LC element based on the targeted lower bound of impedance ($Z_0$), a resonant frequency ($\omega_0$) of the RF fields to be filtered, and known tolerances for the capacitances and inductances of the LC. That is, the tolerances for candidate inductive and capacitive components for use in the LC filter are ascertained. The tolerance for inductors is generally represented herein as $\Delta L/L_0$; whereas the tolerance for capacitors is generally represented herein as $\Delta C/C_0$. For each combination of candidate components, a range of values are identified for $C_0$ that satisfy the condition:

$$C_0 < (1-\Delta L/L_0)/[\omega_0 Z_0(-\Delta C/C_0 + \Delta C/C_0 * \Delta L/L_0 - \Delta L/L_0)] \quad (1)$$

Then, at step 307, a particular value for $C_0$ can be selected within the range of values determined for $C_0$, with a corresponding $L_0$ value then determined based on $L_0=1/(\omega_0^2 * C_0)$.

Alternatively, as shown in FIG. 8, a range of suitable inductance values are first determined, then the corresponding capacitance values are calculated using $C_0=1/(\omega_0^2 * L_0)$. That is, at step 308, a range of suitable central values ($L_0$) are determined for the inductance of the LC element based on $Z_0$, $\omega_0$, $\Delta L/L_0$ and $\Delta C/C_0$. For each combination of candidate components, a range of values are identified for $L_0$ that satisfy the condition:

$$L_0 > Z_0 * (-\Delta C/C_0 + \Delta C/C_0 * \Delta L/L_0 - \Delta L/L_0)/\omega_0(1-\Delta L/L_0). \quad (2)$$

Then, at step 309, a particular value for $L_0$ can be selected within the range of values determined for $L_0$, with a corresponding $C_0$ value then determined based on $C_0 = 1/(\omega_0^2 * L_0)$.

Hence, using the criteria of either Equations (1) or (2), the selection of LC pairs within the ranges of suitable values for $L_0$ and $C_0$ would provide an amplitude of impedance greater than the target value (e.g. greater than the preferred $Z_{MIN}$ of 1000 ohms) with given tolerance as described above. It is useful to examine the ratios of L and C. For the examples of $LC_1$ and $LC_2$ of FIGS. 1-3, the ratio of Z is $Z(LC_2)/Z(LC_1) = C_1/C_2$ or $L_2/L_1$ where L and C are related by $\omega_0 = 1/\text{sqrt}(L_0 C_0)$. This shows that greater L and smaller C yield greater Z. By using the criteria of Z with ±2-5% tolerance, a ratio is 19.4 as calculated as $LC_1$ vs. $LC_2$; $Z(LC_2)/Z(LC_1) = (620/22) * (95/98) * (69/97.5) = 28.2 * 0.97 * 0.71 = 19.4$. For Q values, $Q = 2\pi * fL/Rs$, and the ratio of Q for $LC_2$ and $LC_1$ is $L_2/L_1 * Rs_1/Rs_2$, where $R_S$ refers to parasitic resistance (discussed below.)

In one particular example, with $Z_0 = 1000$ ohms and assuming ±5% tolerance in inductances and capacitances, suitable $C_0/L_0$ combinations are found to be in the range of 19 pF/312.65 nH to 23.7 pF/250.14 nH for a 65.3 MHz/1.5 T MRI and in the range of 12.12 pF/127.61 nH to 4 pF/386.51 nH for a 128 MHz/3.0 T MRI. Table I lists exemplary pairs of suitable $C_0$ and $L_0$ values for 65.3 MHz/1.5 T and Table II lists exemplary pairs of suitable $C_0$ and $L_0$ values for 128 MHz/3.0 T.

TABLE I

| $C_0$ (pF) | $L_0$ (nH) |
|---|---|
| 23.75 | 250.14 |
| 21 | 282.87 |
| 20 | 297.02 |
| 19 | 312.65 |

TABLE II

| $C_0$ (pF) | $L_0$ (nH) |
|---|---|
| 12.12 | 127.61 |
| 11 | 140.55 |
| 10 | 154.60 |
| 9 | 171.78 |
| 8 | 193.25 |
| 7 | 220.86 |
| 6 | 257.67 |
| 5 | 309.21 |
| 4 | 386.51 |

Insofar as Equations (1) and (2) are concerned, the equations may be derived as follows. First, impedance may be represented (in complex form) via:

$$Z = j\omega L/(1-\omega^2 LC) \quad (3)$$

At the resonance frequency of $\omega_0$:

$$\omega_0 = 1/\text{sqrt}(L_0 C_0) \quad (4)$$

Z tends toward $\infty$, i.e. toward infinity. Also, when L and C are slightly offset from the ideal resonant values (i.e., $L = L_0 \pm \Delta L$ and $C = C_0 \pm \Delta C$), equations for Z may be expressed by percentage change, i.e. tolerance. That is, equation (3) can be expressed in terms of $C_0$ or $L_0$ as follows:

$$Z = j(1+\Delta L/L_0)/[\omega_0 C_0(\pm \Delta C/C_0 + C/C_0 * \Delta L/L_0 \pm \Delta L/L_0)] \quad (5)$$

and $$Z = j\omega_0 L_0(1 \pm \Delta L/L_0)/(\pm \Delta C/C_0 + \Delta C/C_0 * \Delta L/L_0 \pm \Delta L/L_0) \quad (6)$$

Taking into account the different combinations expressed by the "±" symbols, there are four combinations of equations. That is, there are several possible values for Z among the various combinations. Herein, $Z_{MIN}$ is defined as the minimum among the combinations of $L0 \pm \Delta L0$ and $C_0 \pm \Delta C$. $Z_{MIN}$ can be expressed as:

$$Z_{MIN} = j(1-\Delta L/L_0)/[\omega_0 C_0(-\Delta C/C_0 + \Delta C/C_0 * \Delta L/L_0 - \Delta L/L_0)] \quad (7)$$

in terms of $C_0$ and tolerance of $L_0$ and $C_0$ or $$Z_{MIN} = j\omega_0 L_0(1-\Delta L/L_0)/(-\Delta C/C_0 + \Delta C/C_0 * \Delta L/L_0 - \Delta L/L_0) \quad (8)$$

in terms of $L_0$ and tolerance of $L_0$ and $C_0$

To ensure adequate impedance, $Z_{MIN}$ should be greater than the target lower bound for impedance, i.e. $|Z_{MIN}| > Z_0$. This condition leads to:

$$C_0 < (1-\Delta L/L_0)/[\Delta_0 Z_0(-\Delta C/C_0 + \Delta C/C_0 * \Delta L/L_0 - \Delta L/L_0)]$$

or $$L_0 > Z_0 * (-\Delta C/C_0 + \Delta C/C_0 * \Delta L/L_0 - \Delta L/L_0)/\Delta_0(1-\Delta L/L_0),$$
is met.

that is, Equations (1) and (2), above, are derived.

The technique of FIG. 7 is applicable, where appropriate, to inductive-capacitive elements having both an inductor and a capacitor as well as to inductive-capacitive elements having an inductor with a parasitic capacitance. In the later case, $C_0$ represents the central capacitance value for the parasitic capacitance.

Turning now to FIG. 9, the selection of L and C pairs is discussed further. At step 310, candidate inductive and capacitive components are identified that have central values for capacitance and inductance within the range of suitable or acceptable values of $C_0$ and $L_0$, such as pairs of components having L and C values as shown in TABLES I and II, and for which $\omega_0 = 1/\text{sqrt}(L_0 C_0)$. That is, particular inductors and capacitors are selected for use in a lead from among candidate components provided by manufacturers that meet these specifications (and which are otherwise suited for use in implantable medical leads). Hence, for a 65.3 MHz/1.5 T example, an inductor providing 297 nH ±5% and a capacitor providing 20 pF ±5% might be selected (i.e. combination $LC_2$ of FIGS. 1-3); whereas an inductor providing 10 nH ±5% and a capacitor providing 620 pF ±5% would not be selected (i.e. combination $LC_1$ of FIGS. 1-3), since the later components do not both fall within the range of suitable values, although both pairs of components theoretically achieve the same resonant frequency of 65.3 MHz.

For the particular examples of $LC_1$ and $LC_2$, Tables III and IV set forth the complex impedance values expected based on tolerances of ±5%.

$LC_1$:

TABLE III

| L | C | Z |
|---|---|---|
| $L_0$: 9.58 | $C_0$: 620 | j31225.83 |
| +ΔL: 10.059 | +ΔC: 651 | j56.57529 |
| −ΔL: 9.101 | −ΔC: 589 | j55.73135 |
| +ΔL: 10.059 | −ΔC: 589 | j128.8228 |
| −ΔL: 9.101 | +ΔC: 651 | j133.4233 |

$LC_2$:

TABLE IV

| L | C | Z |
|---|---|---|
| $L_0$: 270 | $C_0$: 22 | j1892346 |
| +ΔL: 283.5 | +ΔC: 23.1 | j1135.525 |
| −ΔL: 256.5 | −ΔC: 20.9 | j1078.802 |
| +ΔL: 283.5 | +ΔC: 20.9 | j45465.26 |
| −ΔL: 256.5 | −ΔC: 21.945 | j41135.23 |

As shown in the tables, with ±5% tolerance for L and C, the lowest Z for $LC_2$ is j1078.8. In contrast, $LC_1$, the lowest Z is only j55.7. This illustrates the reason for the different heating performance between $LC_1$ and $LC_2$ given that the amplitude of Z needs to be greater than 1000 ohms. That is, even in a worst case for $LC_2$, the minimum impedance of 1000 ohms is still achieved. However, in the worst case for $LC_1$, the minimum impendence is not achieved. Indeed, the resulting impedance is far less than the minimum impedance need to achieve reliable RF filtering. Thus, by selecting components based on Equations (1) and (2), the minimum impedance is achieved, despite variations due to tolerances.

Where possible, a combination of components is selected that are effective in the presence of MRI fields with differing RF frequencies, e.g., both 65.3 MHz/1.5 T MRIs and 128 MHz/3.0 T MRIs. In the particular example of TABLES I and II, such is not possible since there is no overlap in the ranges of capacitances. However, for other parameters (tolerances, impedances, frequencies, etc.), pairs of L and C candidate components might be found that meet the criteria of Equations (1) and (2) for both 65.3 MHz/1.5 T and 128 MHz/3.0 T. Also, it should be understood that the tolerances of different candidate components will typically differ. Some may be ±5%, other ±10%, etc. The tolerances for capacitors need not be the same as that of inductors. Accordingly, given a collection of candidate L and C components having differing tolerances, Equations (1) and (2) may need to be solved for each pair of candidate values using the appropriate tolerance values. That is, a set of tables such as TABLES I and II may need to be generated for each different pair of candidate components, with the optimal L and C components then selected based on an examination of all of the tables. Also, due to practical size restrictions for the inductors and capacitors to be used within a lead, it is important to select components while taking into account mechanical considerations and other practical considerations.

Preferably, parasitic capacitances and parasitic resistances are also taken into account, even in implementations where both an inductor and a capacitor are employed. That is, at step 312, parasitic capacitance ($C_S$) and parasitic resistance ($R_S$) values are determined for the candidate components. At step 314, the resistance of the tip stimulation electrode of the lead in which the LC filter is to be installed is determined. At step 316, select an inductive component from the candidate components that has a sufficiently large inductance to yield a low target parasitic capacitance ($C_S$) and that also has a parasitic resistance ($R_S$) smaller than a resistance of a tip stimulation electrode of the lead. At step 318, a capacitive component is then selected based on the inductance of the selected inductive component, which satisfies $C_0=1/(\omega_0^2 *L_0)$. That is, in addition to satisfying the criteria of Equations (1) and (2) with $\omega_0=1/\sqrt{L_0 C_0}$, the components to be used should also provide a parasitic capacitance less than the tip electrode resistance while also providing for a low parasitic capacitance to achieve a good Q value (where $Q=\omega_0 *L/R_s$ or $Q=\omega_0/C*R_s$.) Hence, if the electrode resistance is 500 ohms, $R_s$ should be much smaller than 500 ohms. Typically, with L in the range of 10-500 nH, Q values are in the range of 10-15 with a DC $R_s$ less than 2 ohms. Preferably, parasitic inductance, capacitance and resistance in the leads are also included in the equivalent circuitry for design purposes.

LC filters designed using the techniques described herein can be exploited for use with a wide variety of leads of implantable medical systems. For the sake of completeness, a detailed description of an exemplary pacer/ICD and lead system will now be provided.

Exemplary Pacer/ICD/Lead System

FIG. 10 provides a simplified diagram of the pacer/ICD of FIG. 4, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 10 is shown in electrical communication with a heart 412 by way of a left atrial lead 420 having an atrial tip electrode 422 and an atrial ring electrode 423 implanted in the atrial appendage. Pacer/ICD 10 is also in electrical communication with the heart by way of a right ventricular lead 430 having, in this embodiment, a ventricular tip electrode 432, a right ventricular ring electrode 434, a right ventricular (RV) coil electrode 436. Typically, the right ventricular lead 430 is transvenously inserted into the heart so as to place the RV coil electrode 436 in the right ventricular apex. Accordingly, the right ventricular lead is capable of receiving cardiac signals, and delivering stimulation in the form of pacing and shock therapy to the right ventricle. An LC filtering element 416, designed as described above, is positioned within lead 430 near tip electrode 432 for use in attenuating high frequency signals so as to reduce lead heating. In the figure, the LC filtering element is shown in phantom lines as it is internal to the lead.

To sense left atrial and ventricular cardiac signals and to provide left chamber pacing therapy, pacer/ICD 10 is coupled to a "coronary sinus" lead 424 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 424 is designed to receive atrial and ventricular cardiac signals and to deliver left ventricular pacing therapy using at least a left ventricular tip electrode 426 and a left ventricular ring electrode 429 and to deliver left atrial pacing therapy using at least a left atrial ring electrode 427, and shocking therapy using at least an SVC coil electrode 428. An LC filtering element 417, designed as described above, is positioned within lead 424 near tip electrode 426 for use in attenuating high frequency signals so as to reduce lead heating. In the figure, the LC filtering element is shown in phantom lines as it is internal to the lead.

With this configuration, biventricular pacing can be performed. Although only three leads are shown in FIG. 10, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 11:
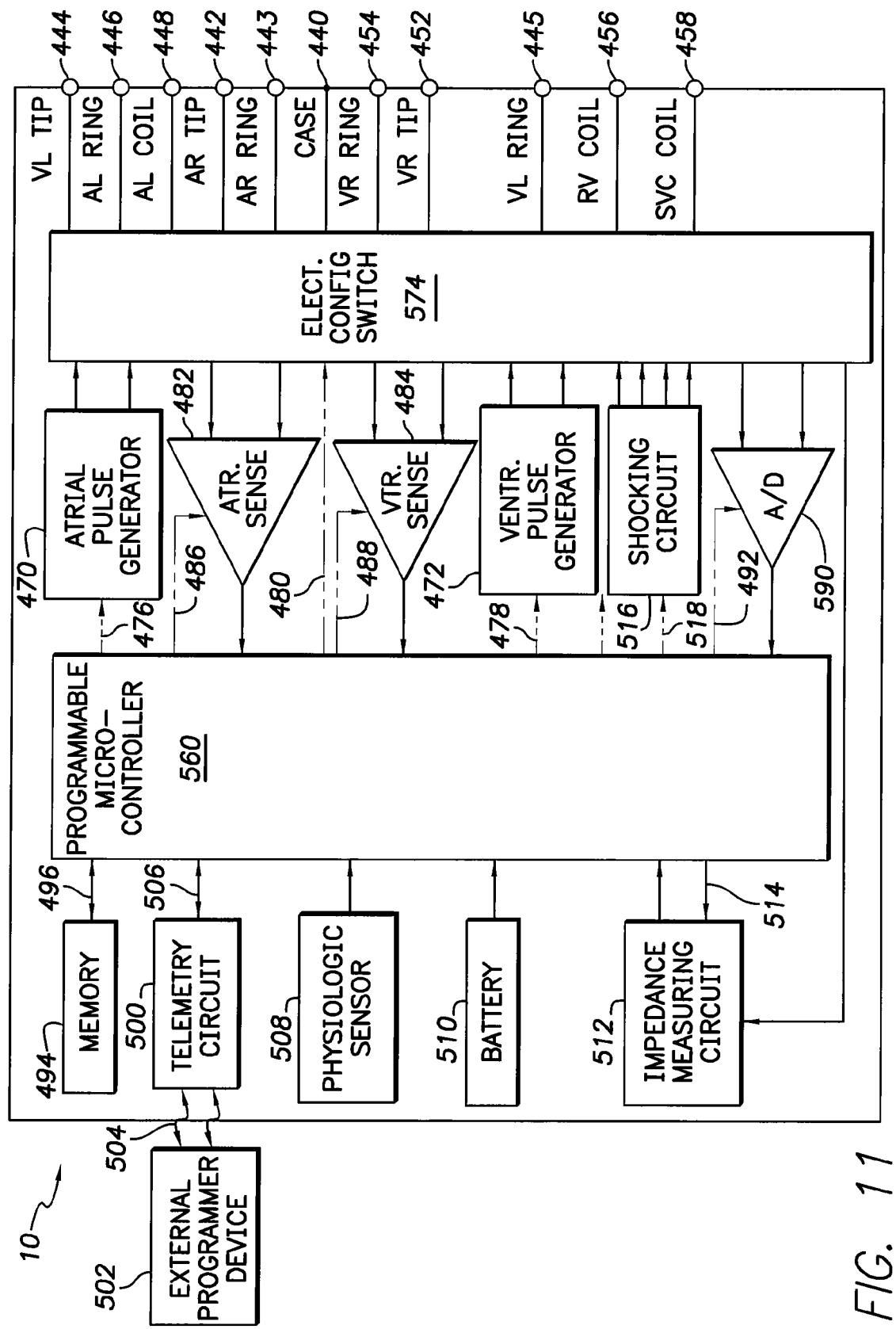
FIG. 11 is a functional block diagram of the pacer/ICD of FIG. 10, illustrating basic circuit elements that provide cardioversion, defibrillation and/or pacing stimulation in four chambers of the heart.

A simplified block diagram of internal components of pacer/ICD 10 is shown in FIG. 11. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 440 for pacer/ICD 10, shown schematically in FIG. 11, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 445, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left ventricular ring terminal ($V_L$ RING) 445, a left atrial ring terminal ($A_L$ RING) 446, and a left atrial shocking terminal ($A_L$ COIL) 448, which are adapted for connection to the left ventricular ring electrode 426, the left atrial tip electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 432, right ventricular ring electrode 434, the RV coil electrode 436, and the SVC coil electrode 438, respectively.

At the core of pacer/ICD 10 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 11, an atrial pulse generator 470 and a ventricular pulse generator 472 generate pacing stimulation pulses for delivery by the right atrial lead 420, the right ventricular lead 430, and/or the coronary sinus lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, coronary sinus lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain and/or sensitivity control enables pacer/ICD 10 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 10 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the coronary sinus lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 494 through a telemetry circuit 500 in telemetric communication with an external device 502, such as a programmer, transtelephonic transceiver or a diagnostic system analyzer, or a bedside monitoring system. The telemetry circuit 500 is activated by the microcontroller by a control signal 506. The telemetry circuit 500 advantageously allows IEGMs and other electrophysiological signals and/or hemodynamic signals and status information relating to the operation of pacer/ICD 10 (as stored in the microcontroller 460 or memory 494) to be sent to the external programmer device 502 through an established communication link 504.

Pacer/ICD 10 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV Delay, V-V Delay, etc.) at which the atrial and ventricular pulse generators, 470 and 472, generate stimulation pulses. While shown as being included within pacer/ICD 10, it is to be understood that the physiologic sensor 508 may also be external to pacer/ICD 10, yet still be implanted within or carried by the patient. A common type of rate responsive sensor is an activity sensor incorporating an accelerometer or a piezoelectric crystal, which is mounted within the housing 440 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG. 11. The battery 510 may vary depending on the capabilities of pacer/ICD 10. If the system only provides low voltage therapy, a lithium iodine or lithium copper fluoride cell may be utilized. For pacer/ICD 10, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 10 is preferably capable of high voltage therapy and appropriate batteries.

As further shown in FIG. 11, pacer/ICD 10 has an impedance measuring circuit 512 which is enabled by the microcontroller 460 via a control signal 514. Various uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, measuring lead resistance, etc. The impedance measuring circuit 120 is advantageously coupled to the switch 54 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-11 joules) or high energy (11 to at least 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 11-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

What have been described are systems and methods for use with pacing/sensing leads for use with a pacer/ICD. Principles of the invention may be exploiting using other implantable systems or in accordance with other techniques. Thus, while the invention has been described with reference to particular exemplary embodiments, modifications can be made thereto without departing from the scope of the invention.

What is claimed is:

1. A method for selecting components for use with an inductive-capacitive (LC) element to reduce heating within a lead of an implantable medical device due to radio-frequency (RF) fields, the method comprising:

determining tolerances for capacitances and inductances of candidate components for the LC element;

determining suitable values for the capacitance and the inductance of the LC element based on an RF frequency to be filtered, the tolerances for the capacitances and the inductances of candidate components of the LC element and a target impedance value for the LC element; and selecting particular components for use in the LC element based on the suitable values for the capacitance and the inductance, wherein determining values for the capacitance and the inductance of the LC element includes determining ranges of suitable values for capacitance by identifying values satisfying the condition that:

$$C_0 < (1-\Delta L/L_0)/[\omega_0 Z_0(-\Delta C/C_0 + \Delta C/C_0 * \Delta L/L_0 - \Delta L/L_0)]$$

where $Z_0$ represents a target lower bound for the impedance, $C_0$ represents a suitable central capacitance value, $L_0$ represents a suitable central inductance value, $\Delta C/C_0$ represents the tolerance of the capacitance of the LC element, $\Delta L/L_0$ represents the tolerance of the inductance of the LC element, and $\omega_0$ represents the resonant frequency, and installing the selected components within a lead of an implantable medical device.

2. The method of claim 1 the target impedance value is a targeted lower bound ($Z_0$) for the amplitude of the impedance for the LC element at the resonant frequency based on the RF fields to be filtered.

3. The method of claim 2 wherein the target impedance is at least 1000 ohms.

4. The method of claim 1 determining the range for inductance of the LC element includes identifying particular combinations of paired $L_0$ and $C_0$ values that satisfy $\omega_0^2 = 1/(C_0 * L_0)$.

5. The method of claim 4 wherein selecting components for use in the LC element based on the suitable values for the capacitance and the inductance includes identifying particular components from among the candidate components having central capacitance and inductance values corresponding to the particular combinations of suitable $L_0$ and $C_0$ values.

6. The method of claim 1 further including employing the lead within a patient.

7. A method for selecting components for use with an inductive-capacitive (LC) element to reduce heating within a lead of an implantable medical device due to radio-frequency (RF) fields, the method comprising:

determining tolerances for capacitances and inductances of candidate components for the LC element;

determining suitable values for the capacitance and the inductance of the LC element based on an RF frequency to be filtered, the tolerances for the capacitances and the inductances of candidate components of the LC element and a target impedance value for the LC element;

selecting particular components for use in the LC element based on the suitable values for the capacitance and the inductance, wherein determining values for the capacitance and the inductance of the LC element includes determining ranges of suitable values for inductance by identifying values satisfying the condition that:

$$L_0 > Z_0 * (-\Delta C/C_0 + \Delta C/C_0 * \Delta L/L_0 - \Delta L/L_0)/\omega_0(1-\Delta L/L_0)$$

where $Z_0$ represents a target lower bound for the impedance, $C_0$ represents a suitable central capacitance value, $L_0$ represents a suitable central inductance value, $\Delta C/C_0$ represents the tolerance of the capacitance of the LC element, $\Delta L/L_0$ represents the tolerance of the inductance of the LC element, $\omega_0$ represents the resonant frequency, and installing the selected components within a lead of an implantable medical device.

8. The method of claim 7 determining the range for capacitance of the LC element further includes identifying particular combinations of paired $L_0$ and $C_0$ values that satisfy $\omega_0^2 = 1/(C_0 * L_0)$.

9. The method of claim 8 wherein selecting components for use in the LC element based on the suitable values for the capacitance and the inductance includes identifying particular components from among the candidate components having central capacitance and inductance values corresponding to the particular combinations of suitable $L_0$ and $C_0$ values.

10. A method for selecting components for use with an inductive-capacitive (LC) element to reduce heating within a lead of an implantable medical device due to radio-frequency (RF) fields, the method comprising:

determining tolerances for capacitances and inductances of candidate components for the LC element;

determining parasitic resistance ($R_s$) values and parasitic capacitance ($C_S$) values for the inductive component of the LC element;

determining suitable values for the capacitance and the inductance of the LC element based on an RF frequency to be filtered, the tolerances for the capacitances and the inductances of candidate components of the LC element, the parasitic resistance values and the parasitic capacitance values for the inductive component of the LC element and a target impedance value for the LC element;

selecting particular components for use in the LC element based on the suitable values for the capacitance and the inductance, and installing the selected components within a lead of an implantable medical device.

11. The method of claim 10 wherein selecting the inductive component based, in part, on the parasitic resistance ($R_s$) values and parasitic capacitance ($C_S$) values includes:

selecting an inductive component having a sufficiently large inductance to yield a target parasitic capacitance ($C_s$) and also having a parasitic resistance ($R_s$) smaller than a resistance of a tip stimulation electrode of the lead.

12. The method of claim 11 wherein selecting the inductive component based, in part, on the parasitic resistance ($R_s$) values and parasitic capacitance ($C_S$) values includes:

selecting an inductive component with a parasitic capacitance ($C_s$) sufficient to achieve a target temperature reduction within the lead in the presence of two or more fields of differing RF frequencies.

13. The method of claim 12 wherein the two or more fields of differing RF frequencies include magnetic resonance imaging (MRI) fields having RF fields of about 65 MHz and MRIs fields having RF fields of about 128 MHz.

* * * * *